(12) United States Patent
Lisanti et al.

(10) Patent No.: US 11,497,749 B2
(45) Date of Patent: Nov. 15, 2022

(54) MITOFLAVOSCINS: TARGETING FLAVIN-CONTAINING ENZYMES ELIMINATES CANCER STEM CELLS (CSCS) BY INHIBITING MITOCHONDRIAL RESPIRATION

(71) Applicant: LUNELLA BIOTECH, INC., Ottawa (CA)

(72) Inventors: Michael P. Lisanti, Fulton, MD (US); Federica Sotgia, Fulton, MD (US)

(73) Assignee: LUNELLA BIOTECH, INC., Ontario (CA)

(*) Notice: Subject to any disclaimer, the term of this patent is extended or adjusted under 35 U.S.C. 154(b) by 0 days.

(21) Appl. No.: 16/758,235

(22) PCT Filed: Oct. 23, 2018

(86) PCT No.: PCT/US2018/057093
§ 371 (c)(1),
(2) Date: Apr. 22, 2020

(87) PCT Pub. No.: WO2019/083997
PCT Pub. Date: May 2, 2019

(65) Prior Publication Data
US 2020/0246344 A1     Aug. 6, 2020

Related U.S. Application Data

(60) Provisional application No. 62/576,287, filed on Oct. 24, 2017.

(51) Int. Cl.
| | |
|---|---|
| A61K 31/525 | (2006.01) |
| A61P 35/00 | (2006.01) |
| A61K 31/03 | (2006.01) |
| A61K 31/14 | (2006.01) |
| A61K 31/155 | (2006.01) |
| A61K 31/201 | (2006.01) |
| G01N 33/50 | (2006.01) |

(52) U.S. Cl.
CPC ............ *A61K 31/525* (2013.01); *A61K 31/03* (2013.01); *A61K 31/14* (2013.01); *A61K 31/155* (2013.01); *A61K 31/201* (2013.01); *A61P 35/00* (2018.01); *G01N 33/5079* (2013.01)

(58) Field of Classification Search
None
See application file for complete search history.

(56) References Cited

U.S. PATENT DOCUMENTS

| | | |
|---|---|---|
| 8,741,853 B2 | 6/2014 | Steliou |
| 2004/0120926 A1 | 6/2004 | Hellstrand et al. |
| 2010/0210569 A1 | 8/2010 | Steliou |
| 2012/0071465 A1 | 3/2012 | Clement et al. |
| 2014/0179660 A1 | 6/2014 | Kim et al. |
| 2015/0254306 A1 | 9/2015 | Musuluri |
| 2016/0075726 A1 | 3/2016 | Neuzil |
| 2016/0339106 A1 | 11/2016 | Shanta |
| 2017/0246195 A1 | 8/2017 | Taylor et al. |

FOREIGN PATENT DOCUMENTS

| | | |
|---|---|---|
| CN | 107137390 | 9/2017 |
| EP | 1 241 002 A2 | 9/2002 |
| JP | H09 309874 A | 12/1997 |
| JP | 2002 221787 A | 8/2002 |
| JP | 2003 207898 | 7/2003 |
| JP | 2005 091713 A | 4/2005 |
| JP | 2009-057330 | 3/2009 |
| RU | 2 522 557 | 7/2014 |
| WO | 00/40229 | 7/2000 |
| WO | WO 2005/061415 A1 | 7/2005 |
| WO | WO 2005/099721 | * 10/2005 |
| WO | WO 2008/145116 | 12/2008 |

OTHER PUBLICATIONS

Arnould et al, Journal of Colloid and Interface Science (2015), vol. 458, pp. 147-154 (Year: 2015).*
Schonfeld et al, Journal of Lipid Research, vol. 57, pp. 943-954 (Year: 2016).*
Zielonka et al., "Mitochondria-Targeted Triphenylphosphonium-Based Compounds: Syntheses, Mechanisms of Action, and Therapeutic and Diagnostic Applications", Americal Chemical Society, Chem. Rev. 2017, 117, pp. 10043-10120.
International Search Report and Written Opinion of the ISA for PCT/US2018/057093, dated Jan. 3, 2019, 18 pages.
Written Opinion of the International Preliminary Examining Authority, dated Apr. 1, 2020, 5 pages.
Comments in Response to International Search Report and Written Opinion dated 23, Aug. 23, 2019, 3 pages.
Amendment Under PCT Article 34 Explanatory Letter, dated Aug. 23, 2019, 2 pages.
Chakraborty et al., "Reaction of Reduced Flavins and Flavoproteins with Diphenyliodonium Chloride", Journal of Biological Chemistry, 2002, vol. 277, No. 44, pp. 41507-41516.
Pryde et al., "Superoxide is Produced by the Reduced Flavin in Mitochondrial Complex I: A Single, Unified Mechanism that Applies During Both Forward and Reverse Electron Transfer", Journal of Biological Chemistry, 2011, vol. 286, No. 20, pp. 18056-18065.
Yagi et al., "Studies on Fatty Acid Esters of Flavins", The Journal of Vitaminology, 1969, vol. 15, pp. 155-159.

(Continued)

*Primary Examiner* — Zinna Northington Davis
(74) *Attorney, Agent, or Firm* — Nixon & Vanderhye, P.C.

(57) ABSTRACT

The present disclosure relates to compounds that bind to flavin-containing enzymes and inhibit mitochondrial function, referred to herein as mitoflavoscins. Methods of screening compounds for mitochondrial inhibition and anti-cancer properties are disclosed. Also described are methods of using mitoflavoscins to prevent or treat cancer, bacterial infections, and pathogenic yeast, as well as methods of using mitoflavoscins to provide anti-aging benefits. Specific mitoflavoscin compounds are also disclosed.

19 Claims, 25 Drawing Sheets

(56) References Cited

OTHER PUBLICATIONS

Schwarz et al., "Identification of the Key Enzyme of Roseflavin Biosynthesis", Angew. Chem. Int. Ed. 2016, vol. 55, pp. 6103-6106.
Wang Ming et al., "Transition-Metal-Free Diarylannulated Sulfide and Selenide Constructions via Radical/Anion-Mediated Sulfur-Iodine and Selenium-Iodine Exchange", Organic Letters, vol. 18, No. 21, Nov. 4, 2016, pp. 5756-5759, XP55820220.
Extended European Search Report for European Application No. EP 18 87 1436 dated Jul. 12, 2021.
Murphy,M.P. (2008): Targeting lipophilic cations to Mitochondria. Biochimica et Biophysica Acta (BBA). Bioenergetics, 1777 (7-8), 1028-1031. doi:10.10.1016/j.bbabio.2008.3.029.
Karlsson, M. et al. (2016) Changes in energy metabolism due to acute rotenoneinduced mitochondrial complex I dysfunction—An in vivo large animal model. Mitochondrion 31, 56-62.
Ozsvari, B. et al. (2017) Mitoketoscins: Novel mitochondrial inhibitors for targeting ketone metabolism in cancer stem cells (CSCs). Oncotarget 8, 78340-50 (Publicado el Sep. 24, 2017).
Bonucceili, G. et al. (2017) NADH autofluorescence, a new metabolic biomarker for cancer stem cells: Identifcation of Vitamin C and CAPE as natural products targeting "sternness". Oncotarget 8, 20667-78.
Hassman, M. et al. (2003) FK866, a Highly Specific Noncompetitive Inhibitor of Nicotinamide Phosphoribosyltransferase, Represents a Novel Mechanism for Induction of Tumor Cell Apoptosis. Cancer Research 63, 7436-42.
Chili Search Report for 202001108 dated Aug. 27, 2021.
Wang et al., "Dual-Targeting Small-Molecule Inhibitors of the Staphylococcus aureus FMN Riboswitch Disrupt Riboflavin Homeostasis in an Infectious Setting", Cell Chemical Biology 24, pp. 576-588, http://dx.doi.org/10.1016/j.chembiol.2017.03.014, May 18, 2017.
Singh G. "Mitochondrial FAD-linked glycerol-3-phosphate dehydrogenase: a target for cancer therapeutics. Pharmaceuticals". Feb. 2014;7(2): 192-206.
Baldwin J. "High-throughput Screening for Potent and Selective Inhibitors of Plasmodium falciparum Dihydroorotate Dehydrogenase". The Journal of Biological Chemistry, vol. 280, No. 23, Issue of Jun. 10, pp. 21847-21853, 2005.

\* cited by examiner

DPI

A

FMN

B

Diphenyleneiodonium chloride

A

Diphenyliodonium chloride

B

DPI

DPI Related

MITOFLAVOSCINS: TARGETING FLAVIN-CONTAINING ENZYMES ELIMINATES CANCER STEM CELLS (CSCS) BY INHIBITING MITOCHONDRIAL RESPIRATION

This application is the U.S. national phase of International Application No. PCT/US2018/057093 filed 23 Oct. 2018, which designated the U.S. and claims the benefit of U.S. Application No. 62/576,287 filed 24 Oct. 2017, the entire contents of each of which are hereby incorporated by reference.

FIELD

The present disclosure relates to "mitoflavoscins," compounds that bind to flavin-containing enzymes and inhibit mitochondrial function, and includes methods for synthesizing mitoflavoscins, methods of using mitoflavoscins to target cancer stem cells, and pharmaceutical compounds for both treating cancer and reducing drug resistance in cancer cells, the pharmaceutical compositions containing one or more mitoflavoscins as the active ingredient. Also disclosed are "mitoflavins"—compounds that are derivatives of riboflavin that inhibit mitochondrial function.

BACKGROUND

Researchers have struggled to develop new anti-cancer treatments. Conventional cancer therapies (e.g. irradiation, alkylating agents such as cyclophosphamide, and anti-metabolites such as 5-Fluorouracil) have attempted to selectively detect and eradicate fast-growing cancer cells by interfering with cellular mechanisms involved in cell growth and DNA replication. Other cancer therapies have used immunotherapies that selectively bind mutant tumor antigens on fast-growing cancer cells (e.g., monoclonal antibodies). Unfortunately, tumors often recur following these therapies at the same or different site(s), indicating that not all cancer cells have been eradicated. Relapse may be due to insufficient chemotherapeutic dosage and/or emergence of cancer clones resistant to therapy. Hence, novel cancer treatment strategies are needed.

Advances in mutational analysis have allowed in-depth study of the genetic mutations that occur during cancer development. Despite having knowledge of the genomic landscape, modern oncology has had difficulty with identifying primary driver mutations across cancer subtypes. The harsh reality appears to be that each patient's tumor is unique, and a single tumor may contain multiple divergent clone cells. What is needed, then, is a new approach that emphasizes commonalities between different cancer types. Targeting the metabolic differences between tumor and normal cells holds promise as a novel cancer treatment strategy. An analysis of transcriptional profiling data from human breast cancer samples revealed more than 95 elevated mRNA transcripts associated with mitochondrial biogenesis and/or mitochondrial translation. Sotgia et al., *Cell Cycle*, 11(23):4390-4401 (2012). Additionally, more than 35 of the 95 upregulated mRNAs encode mitochondrial ribosomal proteins (MRPs). Proteomic analysis of human breast cancer stem cells likewise revealed the significant overexpression of several mitoribosomal proteins as well as other proteins associated with mitochondrial biogenesis. Lamb et al., *Oncotarget*, 5(22):11029-11037 (2014).

Functional inhibition of mitochondrial biogenesis using the off-target effects of certain bacteriostatic antibiotics or OXPHOS inhibitors provides additional evidence that functional mitochondria are required for the propagation of cancer stem cells. The inventors recently showed that a mitochondrial fluorescent dye (MitoTracker) could be effectively used for the enrichment and purification of cancer stem-like cells (CSCs) from a heterogeneous population of living cells. Farnie et al., *Oncotarget*, 6:30272-30486 (2015). Cancer cells with the highest mitochondrial mass had the strongest functional ability to undergo anchorage-independent growth, a characteristic normally associated with metastatic potential. The 'Mito-high' cell sub-population also had the highest tumor-initiating activity in vivo, as shown using pre-clinical models.

SUMMARY

In view of the foregoing background, the inventors focused a search for new metabolic inhibitors of mitochondria by screening a large library of FDA-approved drugs and other related test compounds with known targets and established mechanisms of action. Inventors limited the search to compounds that significantly reduce mitochondrial ATP production, but do not induce cell death (to avoid drugs with acute toxic side-effects). It is an object of this disclosure to identify present methods of identifying mitoflavoscins, compounds that bind to flavin-containing enzymes and inhibit mitochondrial ATP production. It is also an object of this disclosure to identify mitoflavoscins having anti-cancer and antibiotic properties. It is also an object of this disclosure to identify mitoflavoscins having anti-aging properties. It is also an object of this disclosure to identify mitoflavoscins that function as radiosensitizers and photosensitizers. The term "mitoflavoscins" broadly refers to compounds that bind to flavin-containing enzymes and inhibit mitochondrial functions. These compounds therefore may be designed to target and deplete FMN, FAD, and/or riboflavin. The present disclosure further relates to methods of identifying mitoflavoscins, methods of making such mitoflavoscins, and methods of using mitoflavoscins for therapeutic purposes.

Additionally, previously generated data suggests that inhibitors of mitochondrial function that target the mitochondrial ribosome, referred to as "mitoriboscins," may be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances, such as dietary supplements and caloric restriction. Given their mitochondrial inhibition properties, mitoflavoscins may similarly be used to target bacteria and pathogenic yeast, provide anti-aging benefits, function as radiosensitizers and/or photo-sensitizers, sensitize bulk cancer cells and cancer stem cells to chemotherapeutic agents, pharmaceuticals, and/or other natural substances.

Mitoflavoscins may be identified through a convergent approach of high-throughput screening followed by in vitro validation for mitochondrial inhibition. Mitoflavoscins may be rapidly developed by combining in silico drug design with phenotypic drug screening.

DESCRIPTION

The following description illustrates embodiments of the present approach in sufficient detail to enable practice of the present approach. Although the present approach is described with reference to these specific embodiments, it should be appreciated that the present approach may be embodied in different forms, and this description should not be construed as limiting any appended claims to the specific embodiments set forth herein. Rather, these embodiments are provided so that this disclosure will be thorough and complete, and will fully convey the scope of the present approach to those skilled in the art.

Mitochondrial metabolism is an untapped gateway for treating a number of afflictions, ranging from cancer to bacterial and fungal infections to aging. Functional mitochondria are required for the propagation of cancer stem cells. Inhibiting mitochondrial metabolism in cancer cells impedes the propagation of those cells. The present approach explored this gateway by screening a large library of FDA-approved drugs and other related test compounds, with known targets and established mechanisms of action, and further restricted the search to compounds that significantly reduced ATP production, but did not induce cell death, to avoid drugs with acute toxic side-effects.

Figure 1:
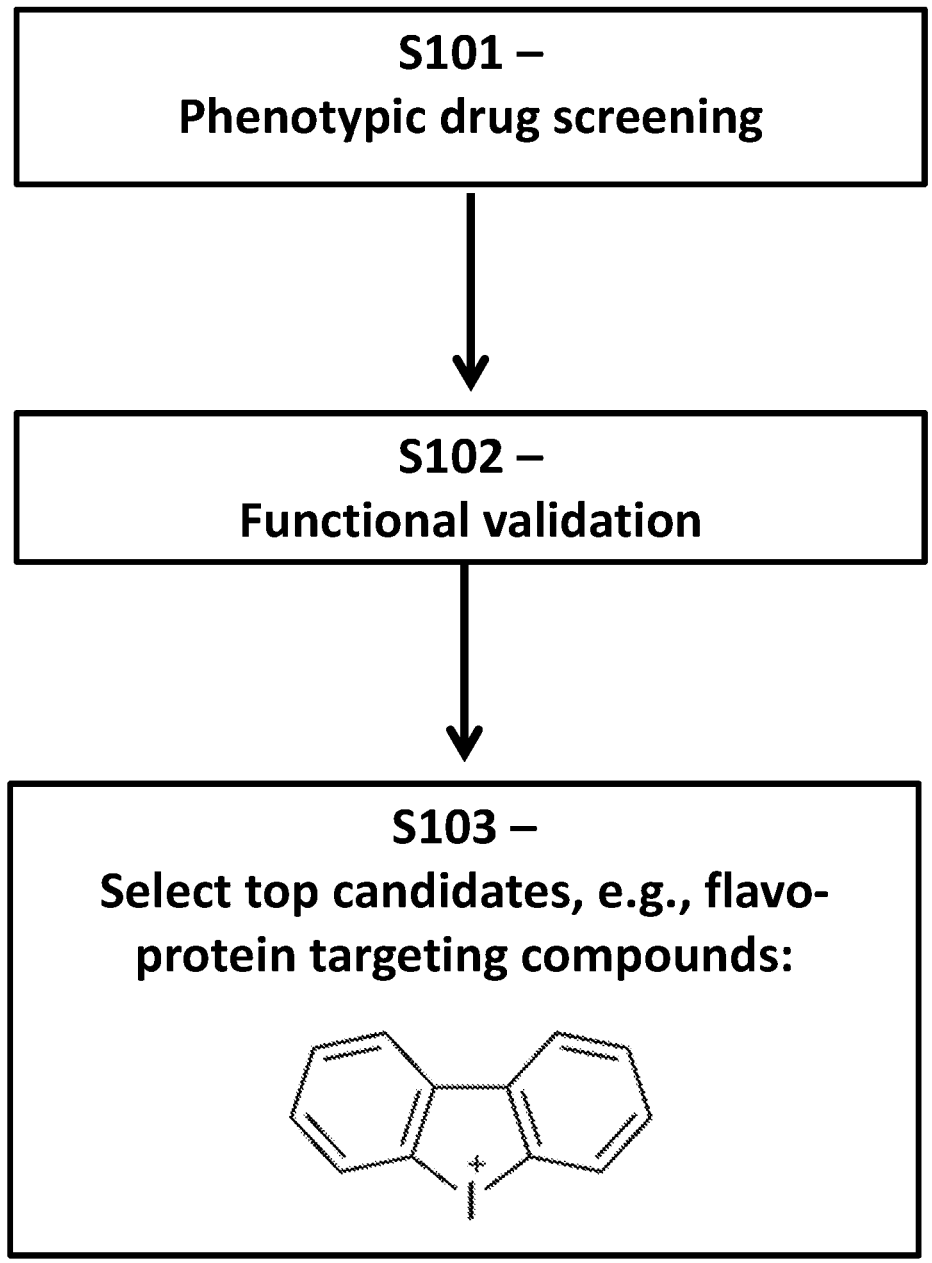
FIG. 1 shows a schematic diagram outlining a drug development strategy according to embodiments of the present approach.

Novel inhibitors of mitochondrial ATP production that bind to flavin-containing enzymes—mitoflavoscins, may be identified through an approach that combines phenotypic drug screening and functional validation. FIG. 1 is an overview of methods for identifying mitoflavoscins by using phenotypic drug screening and functional validation disclosed herein. Embodiments of the method may involve phenotypic drug screening S101 and functional validation S102, and from results selecting one or more candidate drugs S103. Phenotypic drug screening S101 may be conducted using ATP-depletion assays. ATP-depletion assays may identify compounds which may functionally induce ATP depletion without inducing cell death, thereby avoiding toxic side-effects. The screening assay may be performed across a library of molecules. For instance, during the inventors' initial development, MCF7 cells (6,000 cells/well) were plated into black clear-bottom 96-well plates and incubated overnight before treatment. Next, a sub-set of the Tocriscreen™ Compound library (560 compounds) were subjected to phenotypic drug screening at a concentration of 20 μM (Bio-Techne Corp, MN, USA). Compounds were tested after 72 hours of incubation and experiments were performed in triplicate. After treatment, media was aspirated from the wells and plates were washed with warm PBS (supplemented w/$Ca^{2+}$ and $Mg^{2+}$). Then, cells were incubated with a Hoechst 33342 (Sigma) staining solution (10 μg/ml) for 30 min and washed with PBS. Fluorescence was read with a plate reader using excitation/emission wavelengths at 355/460-nm. Then, the CellTiter-Glo luminescent assay (Promega) was performed to measure metabolic activity (ATP content) in the very same wells that were treated with a given compound. Assays were performed according to the manufacturer's protocol. Fluorescence (Hoechst staining) and luminescence intensities (ATP content) were normalized to vehicle-alone treated controls and were displayed as percentages. Positive hits were re-screened at a lower concentration (10 μM) to identify compounds that potently induced ATP-depletion. It should be appreciated that those of skill in the art may choose to employ the same or similar ATP-depletion assays, modify such assays, or may replace the ATP-depletion assay with another methodology for screening selected compounds for mitochondrial inhibition (e.g., oxygen consumption assays).

Figure 2:
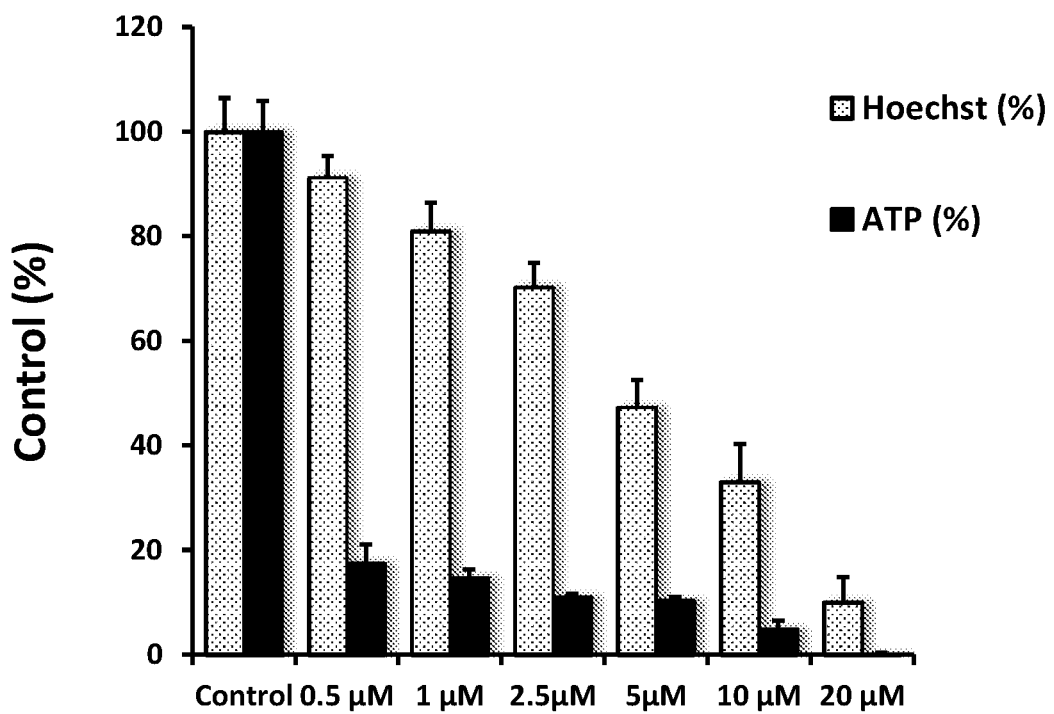
FIG. 2 shows the effects of diphenyleneiodonium chloride (DPI) on ATP levels.

DPI (Diphenyleneiodonium chloride) was identified as a potent inducer of ATP-depletion. The inventors hypothesized that DPI induces ATP-depletion at even lower concentrations. Inventors treated human breast cancer cells (MCF7) with varying concentrations of DPI for 72 hours. Then, the cells were subjected to fluorescent Hoechst DNA-staining to normalize for cell number. By employing CellTiter-Glo as a probe, the inventors were able to use luminescence to measure ATP content in the same wells. At 72 hours of treatment, 500 nM DPI reduced ATP levels by >80%, but did not significantly induce any cell death, as the number of cells attached to the plate remained unchanged (as detected by DNA content). FIG. 2 summarizes these results and demonstrates that DPI selectively depletes ATP levels without inducing massive cell death.

Figure 3A:
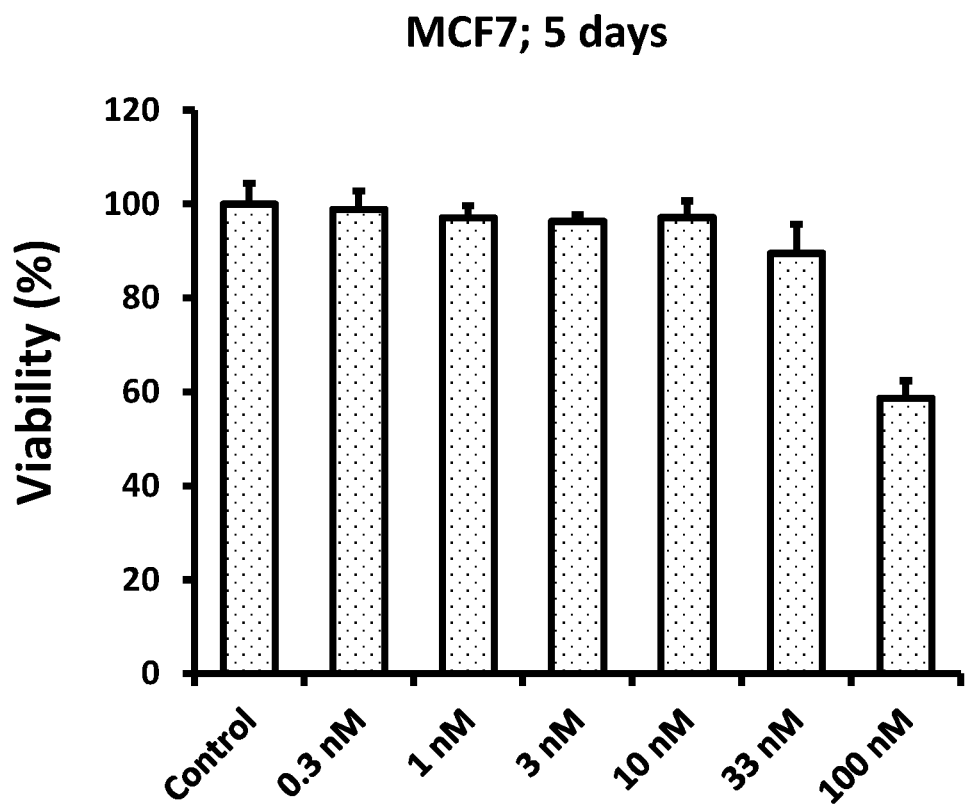
FIG. 3A shows the effects of DPI on cell viability of MCF7 cells.
Figure 3B:
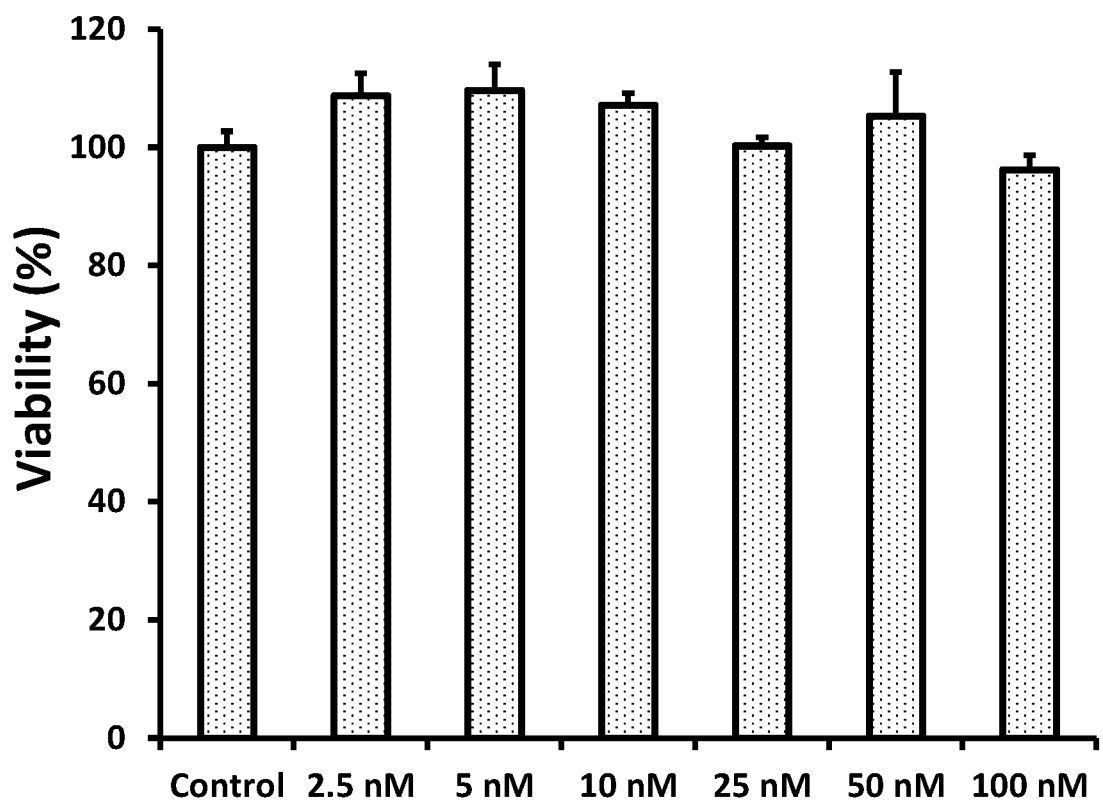
FIG. 3B shows the effects of DPI on cell viability of hTERT-BJ1 cells.

The present approach includes methods of confirming cell viability. Persons of skill in the art may select one or more methods for confirming cell viability suitable for the particular embodiment. The inventors used a Sulphorhodamine (SRB) assay, which is based on the measurement of cellular protein content. After treatment for five days in 96-well plates, cells were fixed with 10% trichloroacetic acid (TCA)

for 1 hour in the cold room, and were dried overnight at room temperature. Then, cells were incubated with SRB for 15 min, washed twice with 1% acetic acid, and air dried for at least 1 hour. Finally, the protein-bound dye was dissolved in a 10 mM Tris, pH 8.8 solution and read using the plate reader at 540-nm. FIG. 3A shows the effects of DPI on cell viability of MCF7 cells. In particular, the data shows that DPI does not significantly affect cell viability, even after five days of treatment. DPI showed little or no toxicity in MCF7 cells, at a concentration as high as 33 nM. FIG. 3B shows the effects of DPI on cell viability of hTERT-BJ1 cells. Virtually identical results were also obtained with normal fibroblasts (hTERT-BJ1), which showed little or no toxic effects, at up to 100 nM, after five days of incubation (FIG. 3B).

The present approach further involves methods of functional validation S102, during which a compound's function as a mitochondrial inhibitor may be confirmed. A number of methods may be used for functional validation, including, for example, metabolic flux analysis, mammosphere assays, viability assays, and antibiotic (anti-bacterial and/or anti-fungal) activity. The inventors determined real-time oxygen consumption rates (OCR) and extracellular acidification rates (ECAR) in MCF7 cells using the Seahorse Extracellular Flux (XF96) analyzer (Seahorse Bioscience, Mass., USA). Briefly, MCF7 cells were maintained in DMEM supplemented with 10% FBS (fetal bovine serum), 2 mM GlutaMAX, and 1% Pen-Strep. 8,000 cells per well were seeded into XF96-well cell culture plates, and incubated overnight at 37° C. in a 5% $CO_2$ humidified atmosphere. The next day, cells were washed in pre-warmed XF assay media (for OCR measurement, XF assay media was supplemented with 10 mM glucose, 1 mM Pyruvate and adjusted at pH 7.4). Cells were then maintained in 175 µL/well of XF assay media at 37° C., in a non-CO2 incubator for 1 hour. During incubation, 25 µL of 80 mM glucose, 9 µM oligomycin, 1M 2-deoxyglucose (for ECAR measurement) and 25 µL of 10 µM oligomycin, 9 µM FCCP, 10 µM rotenone, 10 µM antimycin A (for OCR measurement) in XF assay media was loaded into the injection ports of the XFe-96 sensor cartridge. During the experiment, the instrument injected these inhibitors into the wells at a given time point, while ECAR/OCR was measured continuously. ECAR and OCR measurements were normalized by protein content (Sulphorhodamine B assay). Data sets were analyzed by XFe-96 software, using one-way ANOVA and Student's t-test calculations. All experiments were performed in triplicate.

Figure 4A:
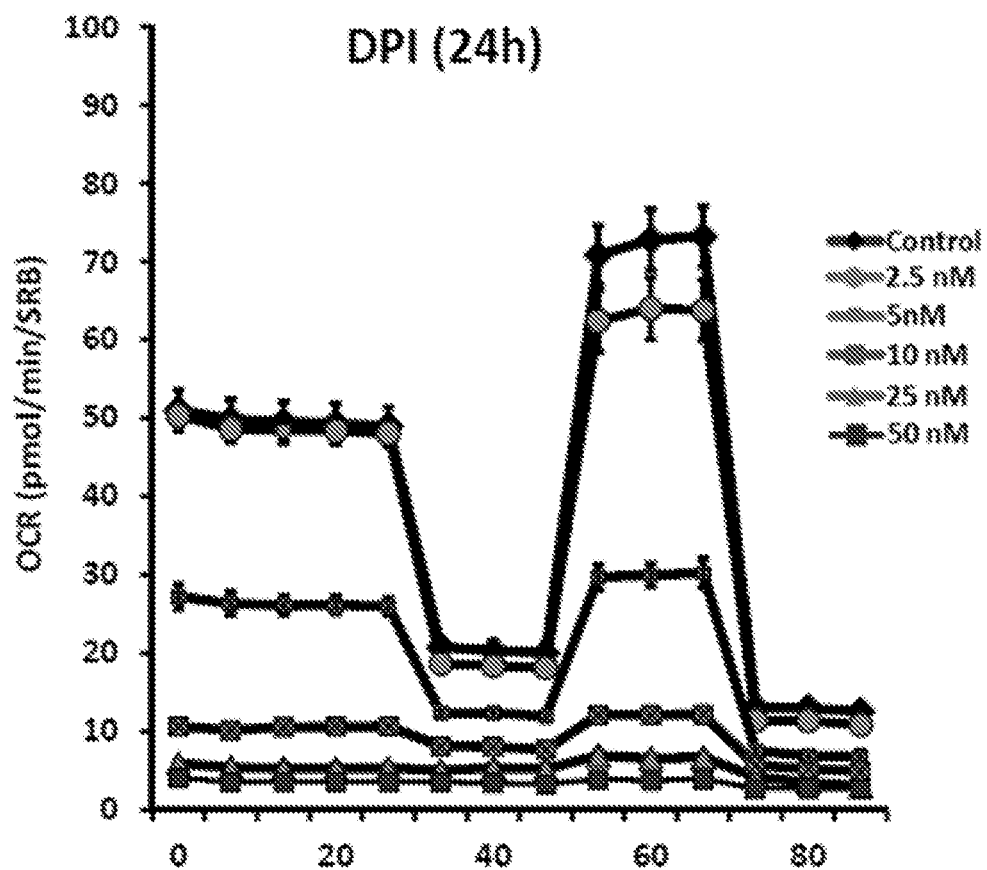
FIG. 4A shows the effects of 24-hour treatment with DPI on oxygen consumption rate (OCR).
Figure 4B:
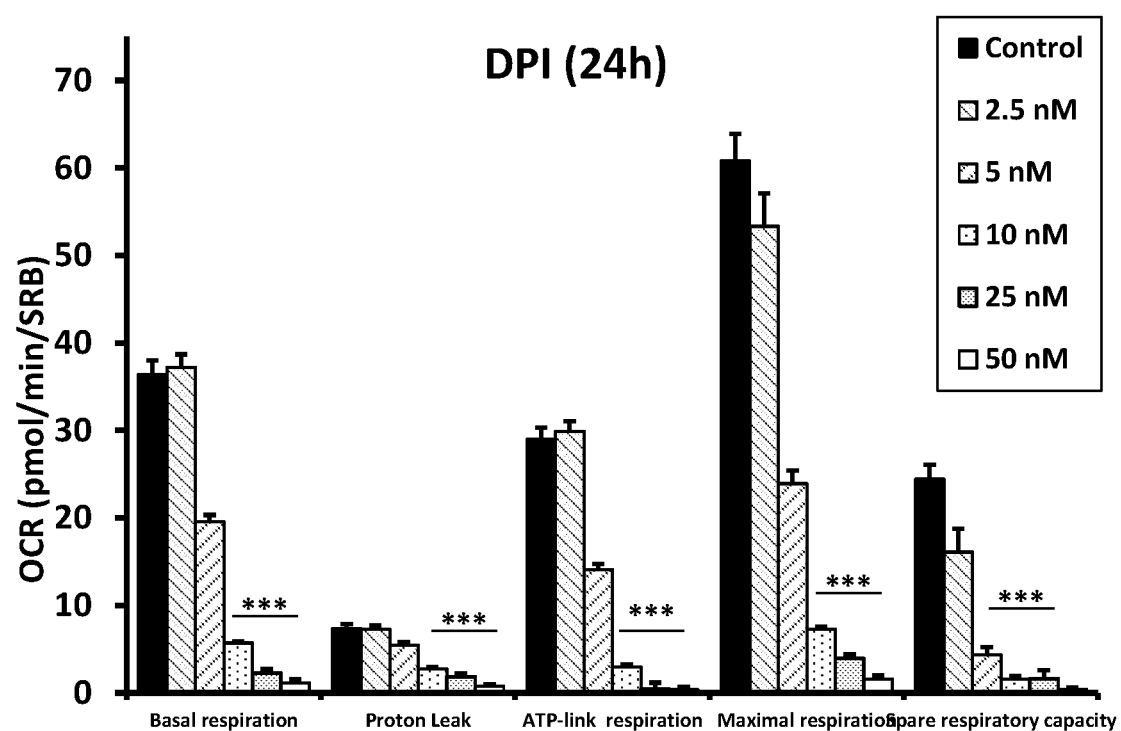
FIG. 4B shows the effects of DPI on basal respiration, proton leak, ATP-linked respiration, maximal respiration, and spare respiratory capacity.

OCR results show that DPI had little or no effect at a concentration of 2.5 nM. However, at 5 nM, basal respiration was reduced by ~50%. Finally, at 10 nM, the basal respiration rate was decreased by ~85%, resulting in a >90% reduction in ATP production. FIG. 4A-B summarizes these results and illustrates that DPI potently inhibits mitochondrial respiration. FIG. 4A shows the effects of DPI treatment on OCR over time, and FIG. 4B shows the effects of DPI treatment on basal respiration, proton leak, ATP-linked respiration, maximal respiration, and spare respiratory capacity. It should be appreciated that numerous methods are known for functional validation, and that persons of skill in the art may select one or more depending on the validation needs (e.g., other assays that measure or approximate mitochondrial function).

Figure 5A:
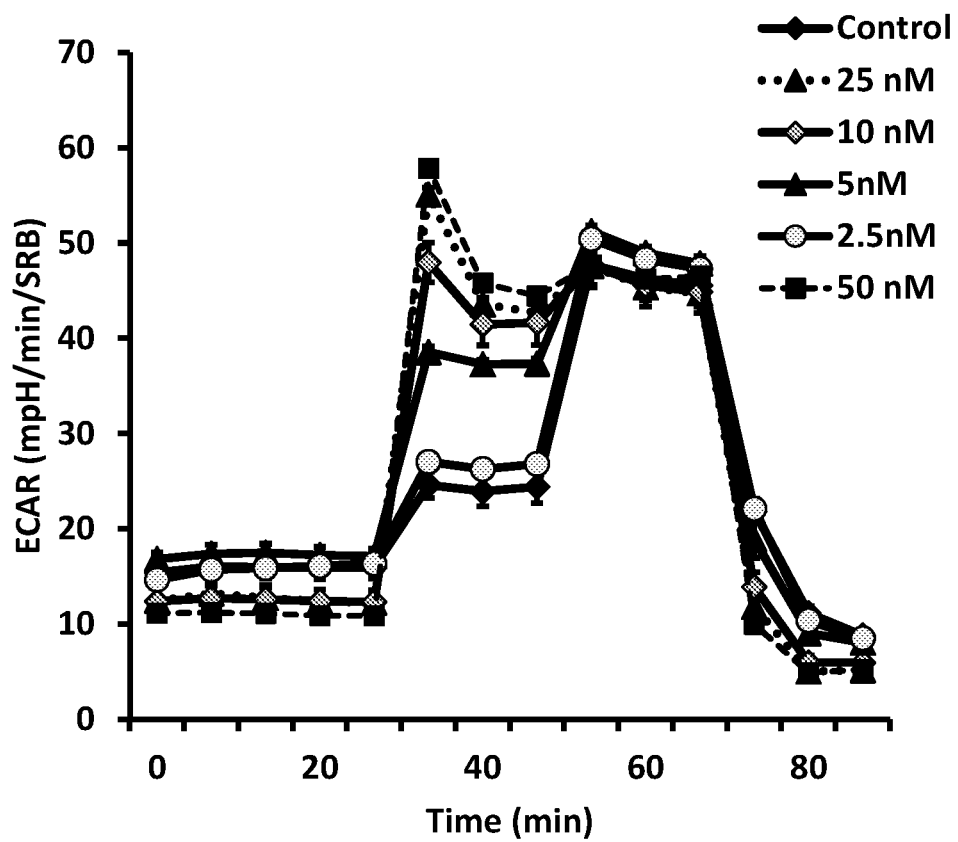
FIG. 5A shows the effects of 24-hour treatment with DPI on extracellular acidification rate (SCAR).
Figure 5B:
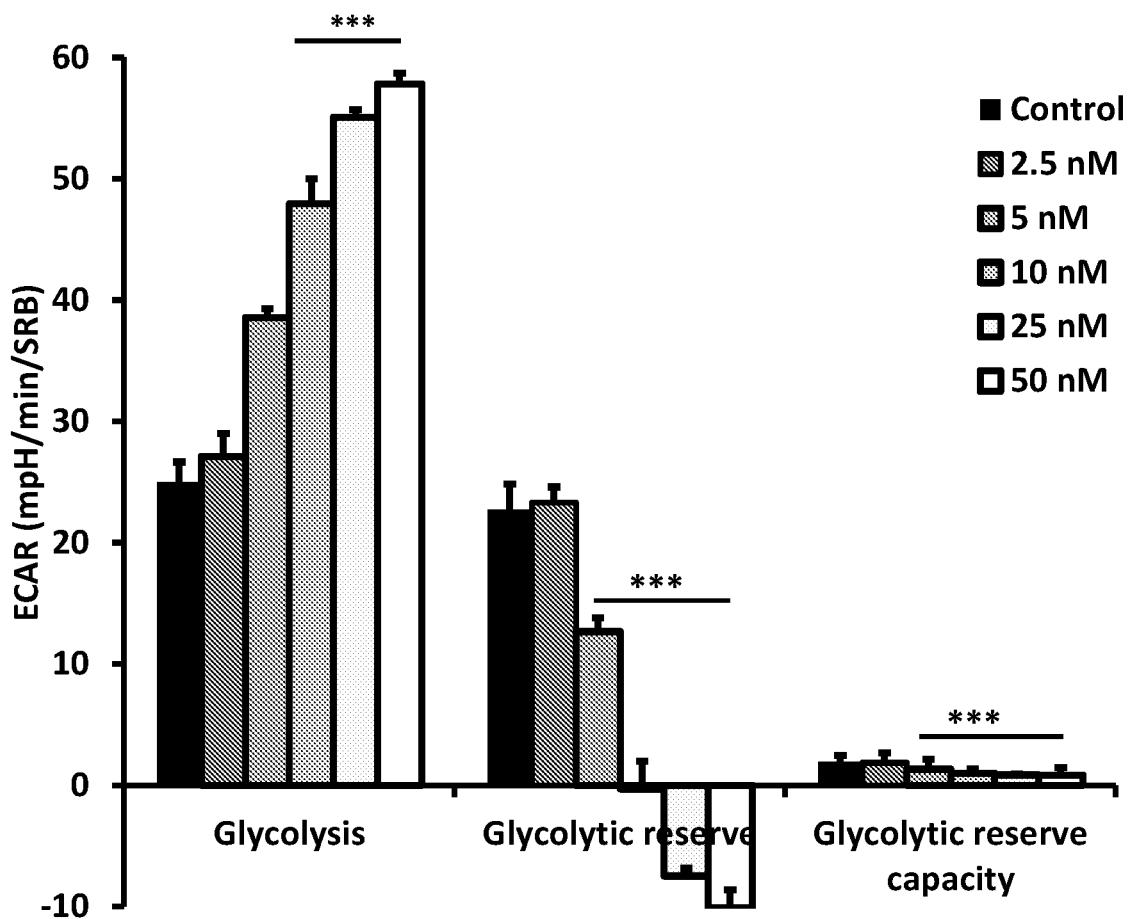
FIG. 5B shows the effects of DPI on glycolysis, glycolytic reserve, non-glucose derived ECAR, and glycolytic reserve capacity.

As mentioned, to determine if the anti-mitochondrial effects of DPI induce a reactive glycolytic response, the inventors subjected DPI-treated breast cancer cells to a "glycolytic stress test" by determining ECAR. MCF7 cells were subjected to metabolic flux analysis with the Seahorse XFe96, which also measures ECAR as a surrogate marker for L-lactate production. After 24 hours of treatment with DPI (2.5 nM), little or no effect was observed. However, at 10 nM DPI, glycolysis was increased by ~2-fold. FIG. 5A-B highlights that DPI potently induced a glycolytic phenotype. FIG. 5A shows the effects of DPI on ECAR over time. FIG. 5B shows the effects of DPI on glycolysis, glycolytic reserve, and glycolytic reserve capacity.

Figure 6:
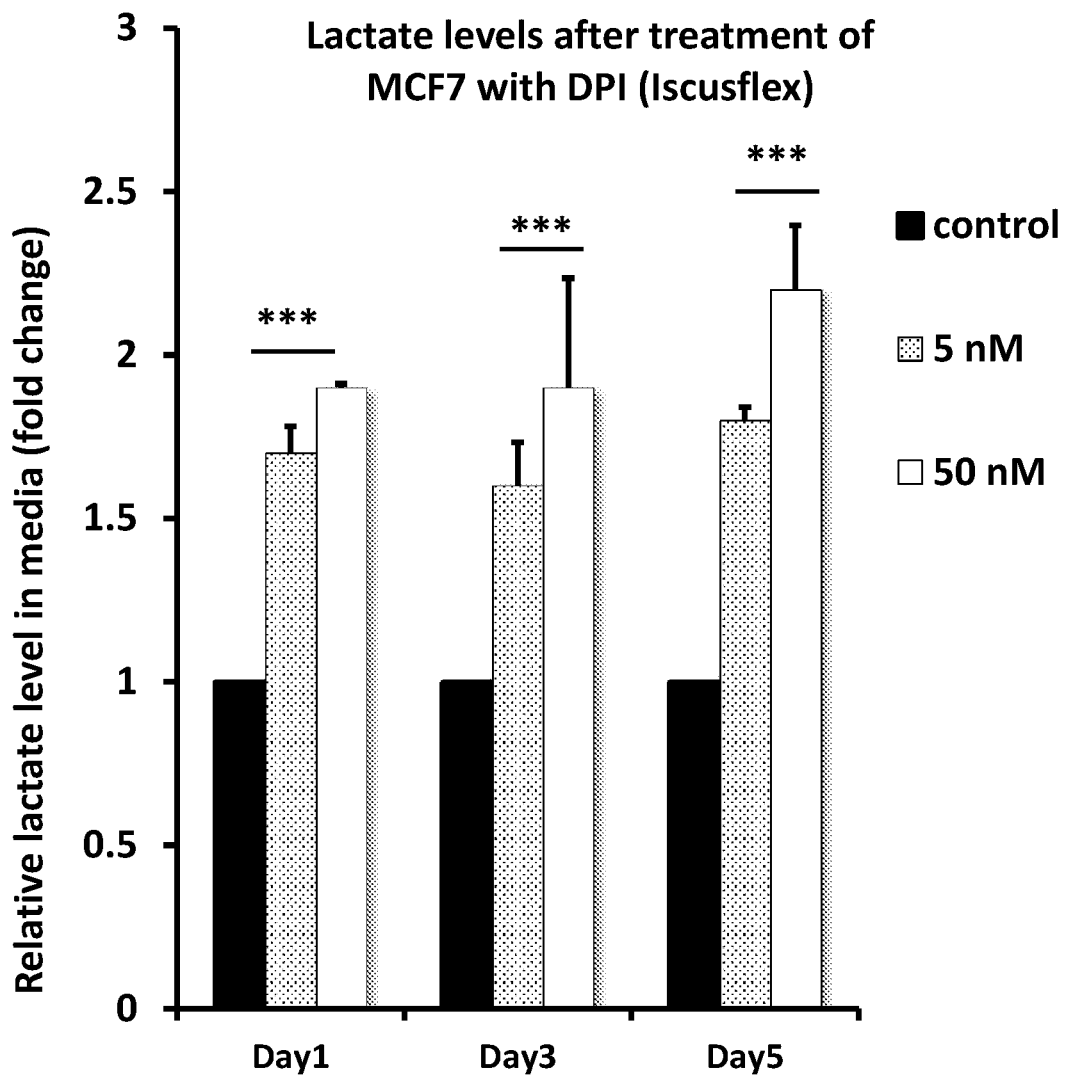
FIG. 6 shows the effects of DPI on L-lactate production.

To confirm that the observed increase in ECAR corresponded to L-lactate production, L-lactate levels were measured directly using the ISCUS$^{flex}$ Microdialysis Analyser (M Dialysis Inc., MA, USA). Culture media were collected, centrifuged and analysed with the ISCUS$^{flex}$ Microdialysis Analyzer after treatment of MCF7 cells with various concentrations of DPI for 1, 3 or 5 days. Calibration of the instrument was performed by samples provided by the manufacturer. Then L-lactate levels were measured and normalized to samples taken from MCF7 cells treated with vehicle only. FIG. 6 shows that DPI induced significant L-lactate production, nearly doubling the amount of lactate produced, consistent with a 2-fold increase in glycolysis.

Figure 7:
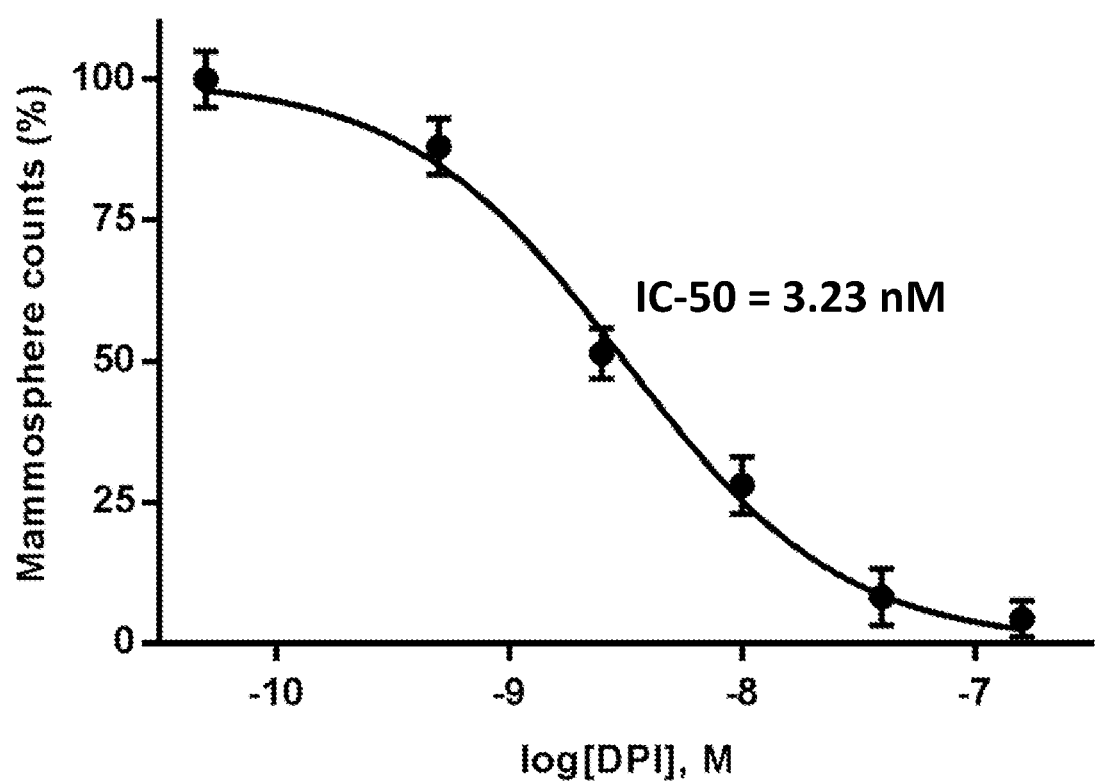
FIG. 7 shows the effects of DPI on mammosphere formation.

The present approach may, in some embodiments, involve methods of testing compounds for anti-cancer properties. For example, the inventors examined the ability of DPI to inhibit mammosphere formation in MCF7 cells. A single cell suspension of MCF7 cells was prepared using enzymatic (1× Trypsin-EDTA, Sigma Aldrich) and manual disaggregation (25-gauge needle). Cells were then plated at a density of 500 cells/cm$^2$ in mammosphere medium (DMEM-F12/B27/20-ng/ml EGF/PenStrep) in non-adherent conditions, in culture dishes coated with (2-hydroxyethylmethacrylate) (poly-HEMA, Sigma). Cells were grown for 5 days and maintained in a humidified incubator at 37° C. at an atmospheric pressure in 5% (v/v) carbon dioxide/air. After 5 days in culture, spheres >50 µm were counted using an eye-piece graticule, and the percentage of cells plated which formed spheres was calculated and is referred to as percent mammosphere formation, normalized to vehicle-alone treated controls. Mammosphere assays were performed in triplicate and repeated three times independently. FIG. 7 highlights that DPI dose-dependently inhibited CSC propagation in the mammosphere assay. DPI treatment significantly reduced CSC propagation, in a concentration-dependent manner, with an IC-50 of 3.23 nM. It should be appreciated that those skilled in the art may use other methods known in the art for assessing a candidate mitoflavoscin's effects on a particular cell line without departing from the present approach. It should also be appreciated that those skilled in the art may assess a candidate mitoflavoscin's effects on other cancer types, as the inhibitors target cancer stem cells (CSCs). CSCs show conserved or similar features across most cancer types.

Figure 8A:
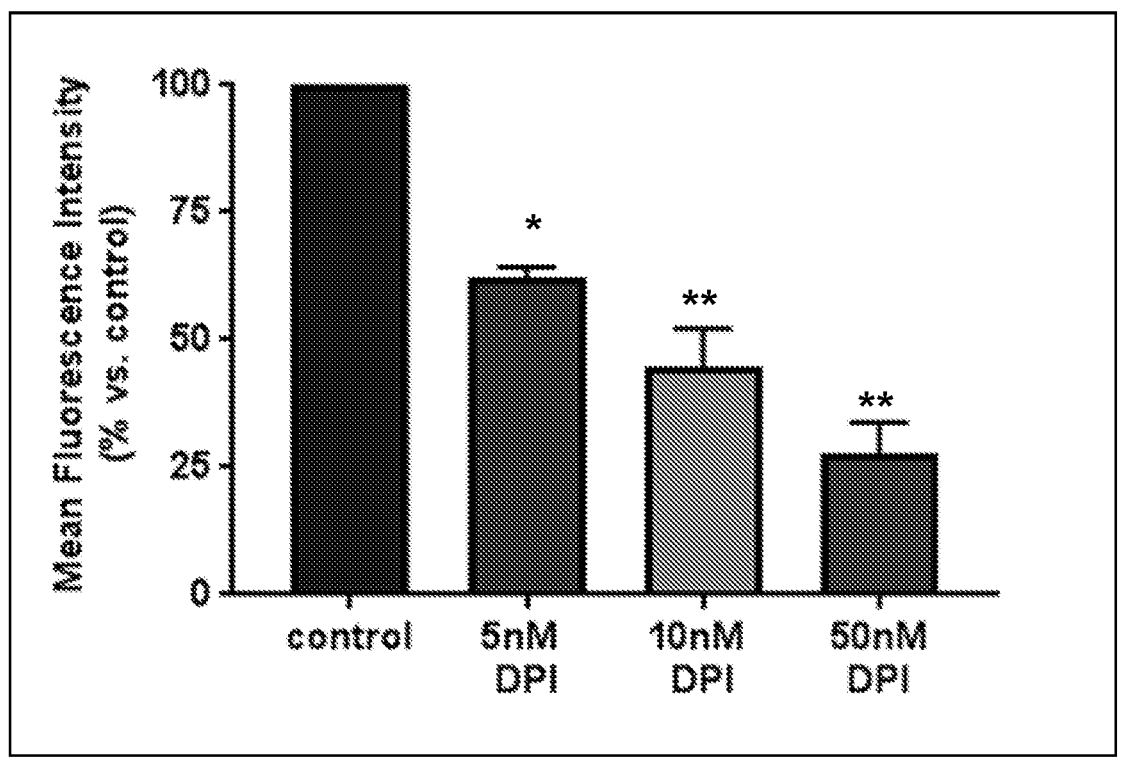
FIGS. 8A and 8B show the effects of DPI on cancer stem cell marker CD44+/CD24−.
Figure 8B:
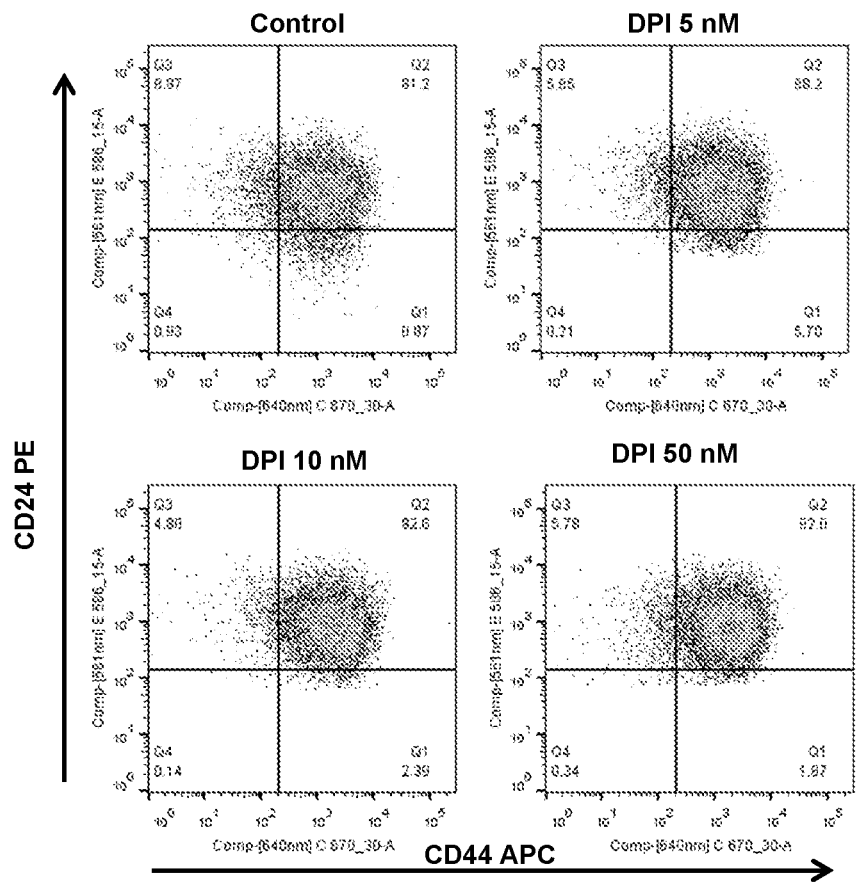

To further validate the findings, the inventors used a second independent approach to quantify "sternness" in cancer cells. Inventors examined specific cell surface markers, namely fluorescent antibody probes directed against CD44 and CD24. The CD44+/CD24-cell population represents a CSC-enriched fraction. 1×10$^5$ MCF7 cells were plated in 6-well plates in complete media supplemented with 10% heat-inactivated FBS. The next day, cells were treated with DPI (5, 10, 50 nM) for 5 days. Vehicle alone (DMSO) control cells were processed in parallel. Briefly, 30,000-50,000 live cells, as identified by 7-AAD dye staining, were analyzed for CD24/CD44 expression. Inventors used CD24 (IOTest CD24-PE, Beckman Coulter) and CD44 (APC mouse Anti-Human CD44, BD Pharmingen) antibodies for fluorescence activated cell sorting (FACS) analysis, using the BD LSR Fortessa (BD Bioscience). Results are the average of three biological replicates (repeats) and are expressed as percentages of mean fluorescence intensity, normalized to the control. One-way ANOVA was used with Bonferroi's multiple comparisons test. FIGS. 8A and 8B show that DPI selectively eliminates these CSCs from the total cell population. The CD44+/CD24− cell population was dose-dependently reduced by DPI treatment, with an IC-50 of 10 nM. It should be appreciated that other methods are known for quantifying sternness in cancer cells, and that persons of skill in the art may select one or more depending on the validation needs.

Figure 9:
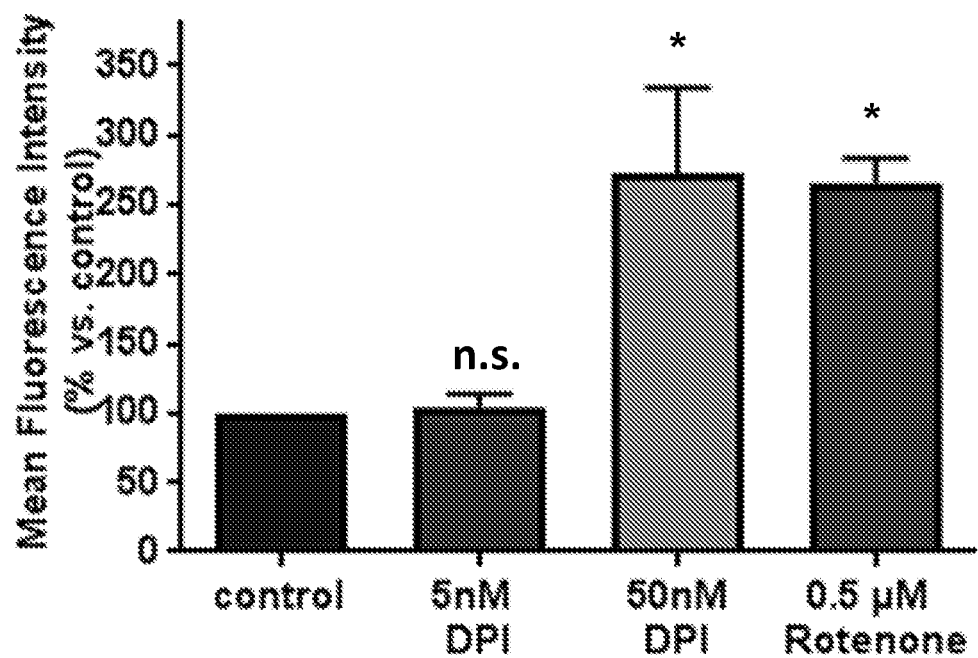
FIG. 9 shows the effects of DPI on mitochondrial reactive oxygen species (ROS) production.

Inventors hypothesized that possible mechanism by which DPI inhibits CSC propagation is by inducing mitochondrial reactive oxygen species (ROS) production. To test this hypothesis, inventors determined the effects of DPI on mitochondrial ROS production, over the range of 5 to 50 nM. Briefly, production of superoxide by mitochondria was measured by the MitoSOX™ Red mitochondrial superoxide indicator (ThermoFisher Sci., M36008). $3 \times 10^5$ MCF7 cells/well were plated in 6-well plates in complete media supplemented with 10% heat-inactivated FBS. The next day, cells were treated with DPI (5, 50 nM) or Rotenone (0.5 μM) for 24 hours. Vehicle alone (DMSO) for control cells were processed in parallel. At least 30,000 events were recorded by FACS using Fortessa (BD Bioscience). Three biological replicates (repeats) were analyzed in independent experiments. Results are the average of the mean of each experiment and are expressed as percentages of mean fluorescence intensity normalized to control. FIG. 9 shows that, at a concentration of 5 nM, DPI failed to induce any detectable mitochondrial ROS production, relative to control cells, treated with vehicle alone. However, 50 nM DPI induced the same amount of mitochondrial ROS as 500 nM Rotenone, which served as a positive control. Therefore, the same concentration of DPI (5 nM) that inhibited mammosphere formation by >50% failed to increase mitochondrial ROS production. As such, the effects of low-dose DPI on "sternness" in cancer cells cannot be explained simply by ROS production.

Figure 10:
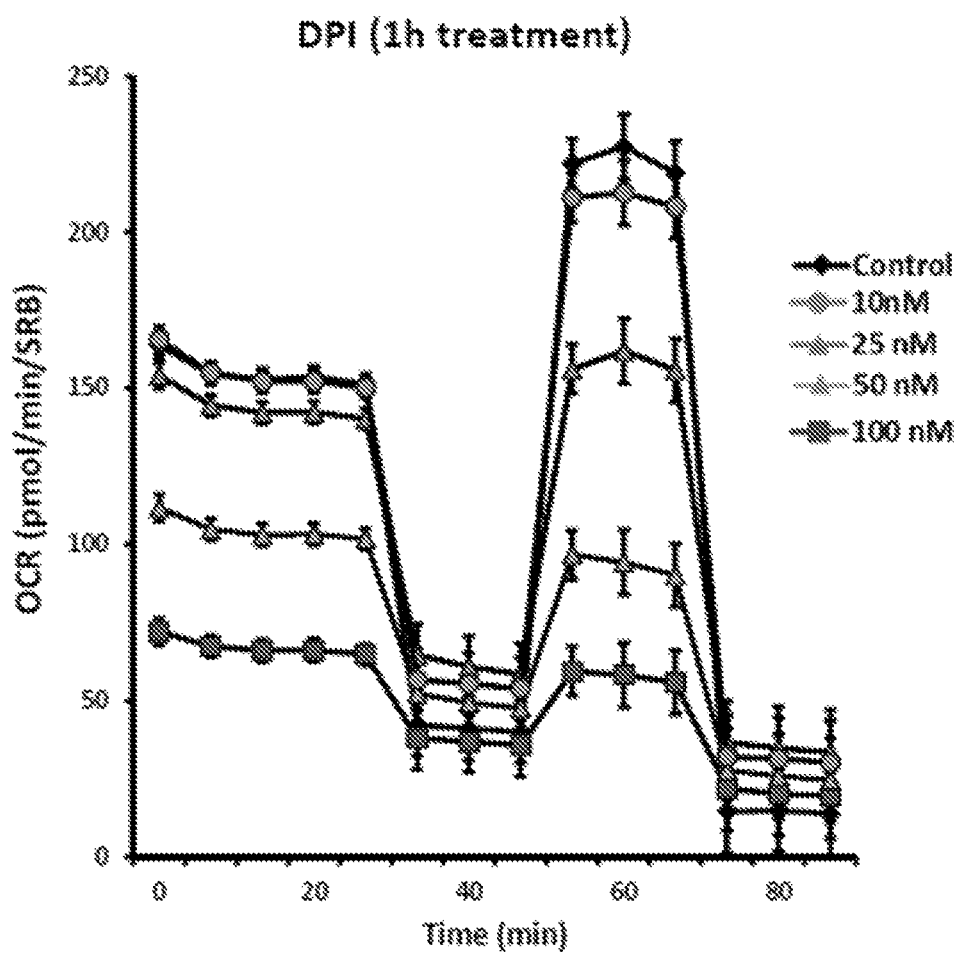
FIG. 10 shows the effects of a one-hour treatment with DPI on OCR.
Figure 11:
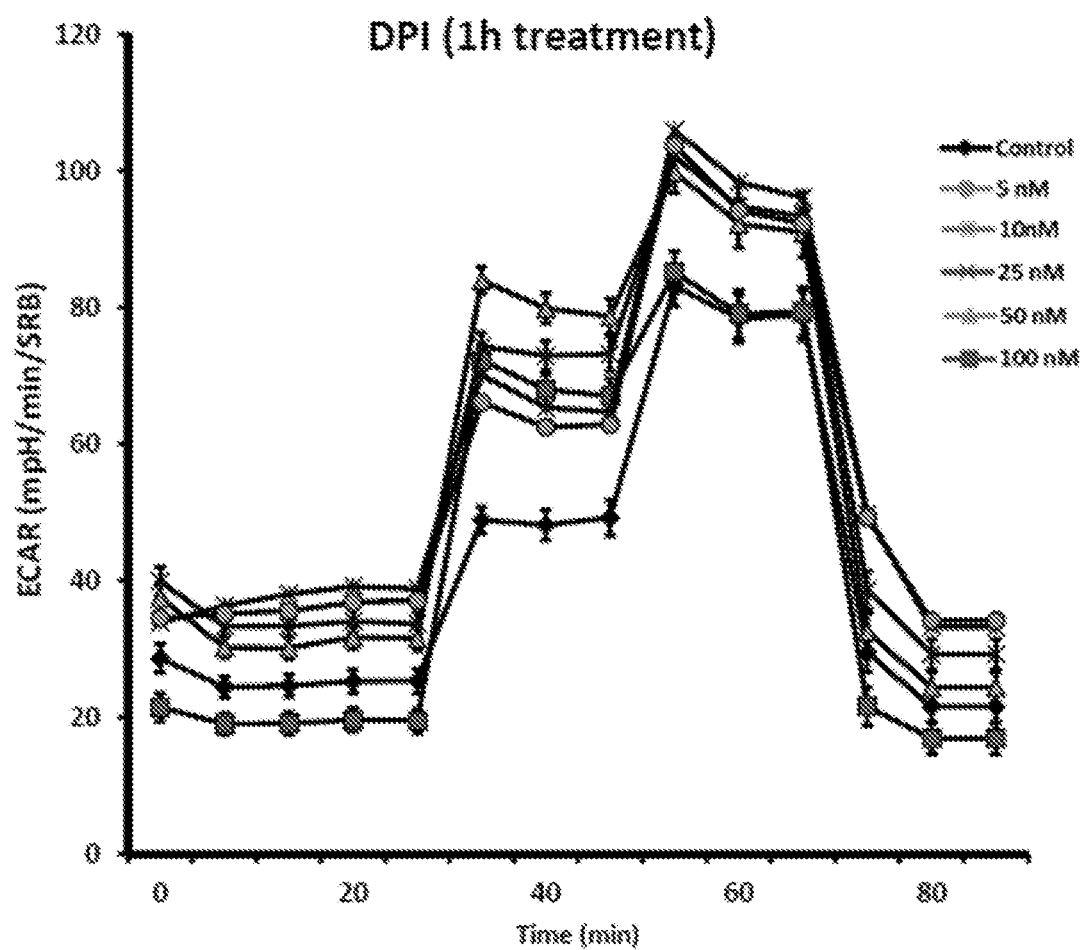
FIG. 11 shows the effects of one-hour treatment with DPI on ECAR.

Given DPI's high potency, inventors assessed its ability to rapidly affect cell metabolism. FIG. 10 demonstrates the fast action of DPI on mitochondrial respiration. After as little as one hour of DPI treatment, the mitochondrial OCR was progressively reduced, over a concentration range of 10 to 100 nM. Basal respiration was inhibited with an IC-50 of 50 nM. Similarly, DPI rapidly induced a reactive glycolytic phenotype. Glycolysis was progressively increased, over a concentration range of 5 to 100 nM. FIG. 11 shows that glycolysis was effectively doubled.

Figure 12A:
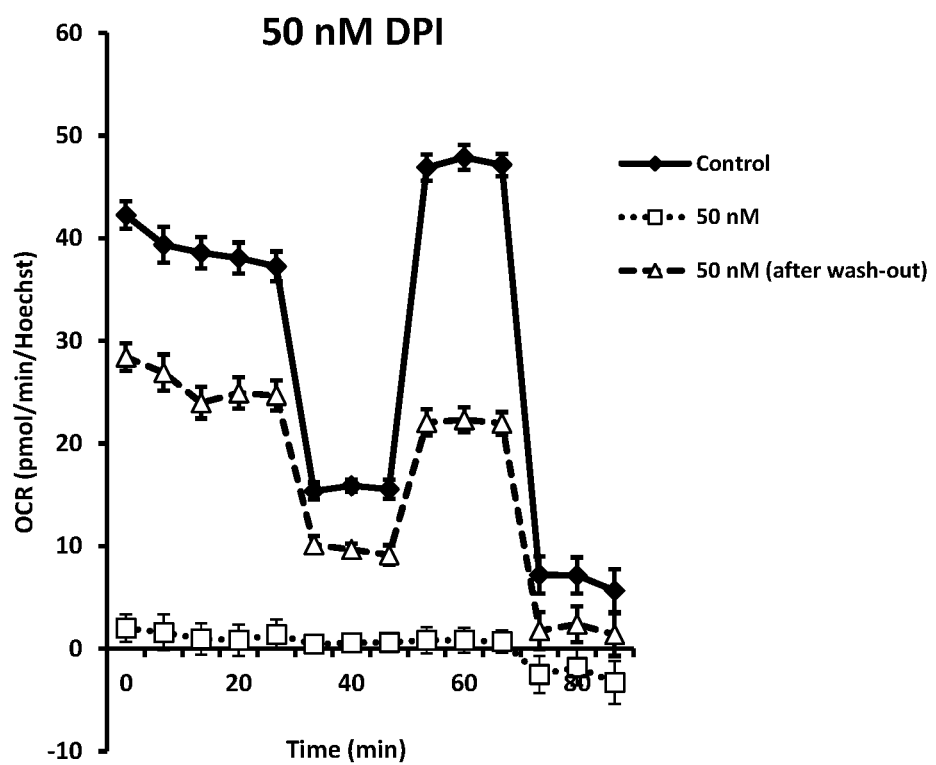
FIGS. 12A-C show the effects of DPI treatment, "wash-out", and recovery on OCR.
Figure 12B:
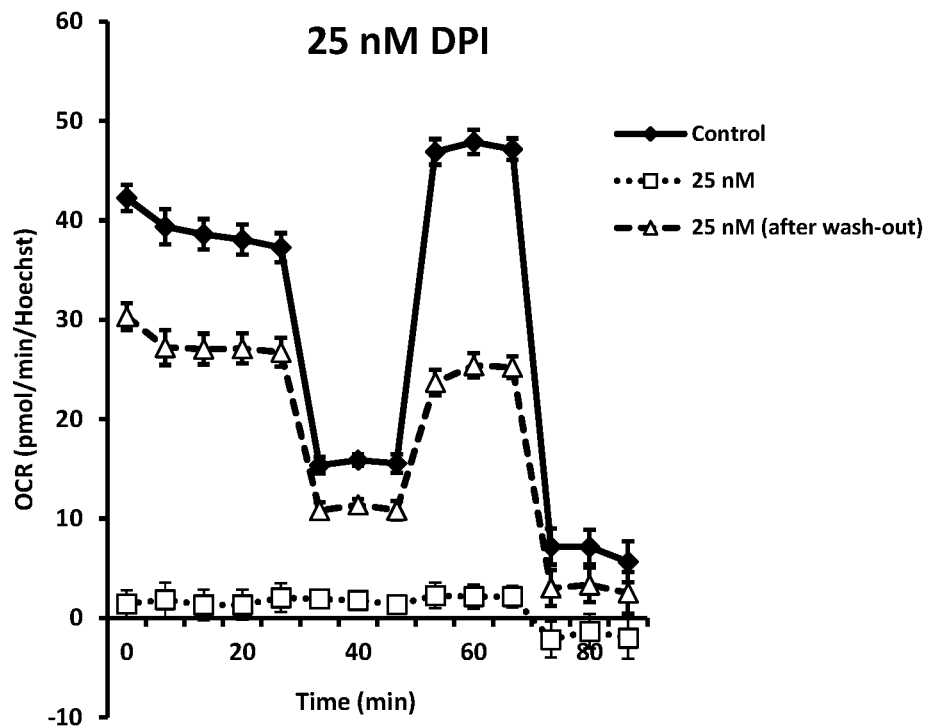
Figure 12C:
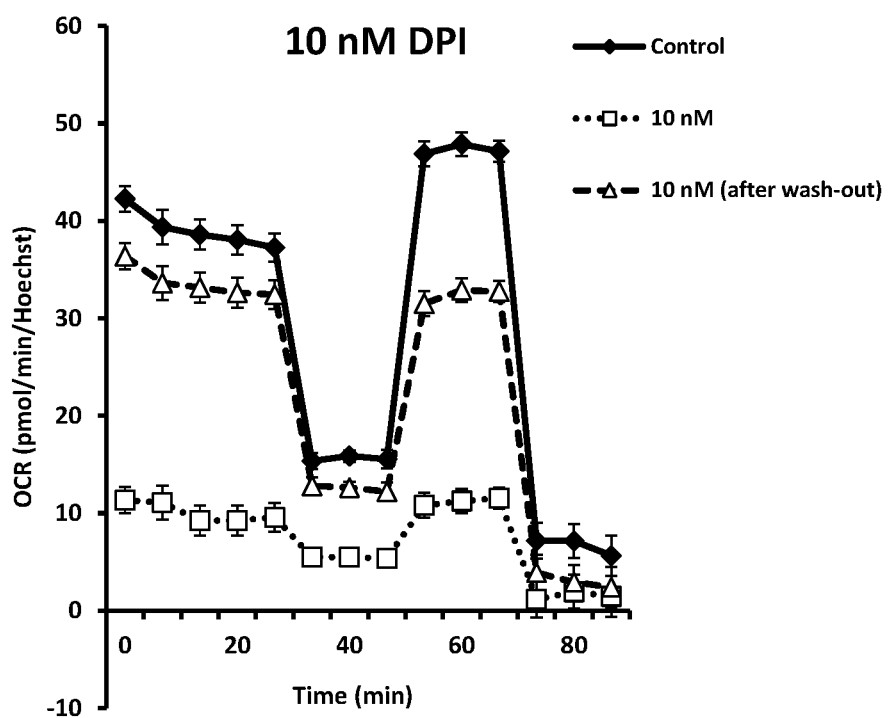
Figure 13:
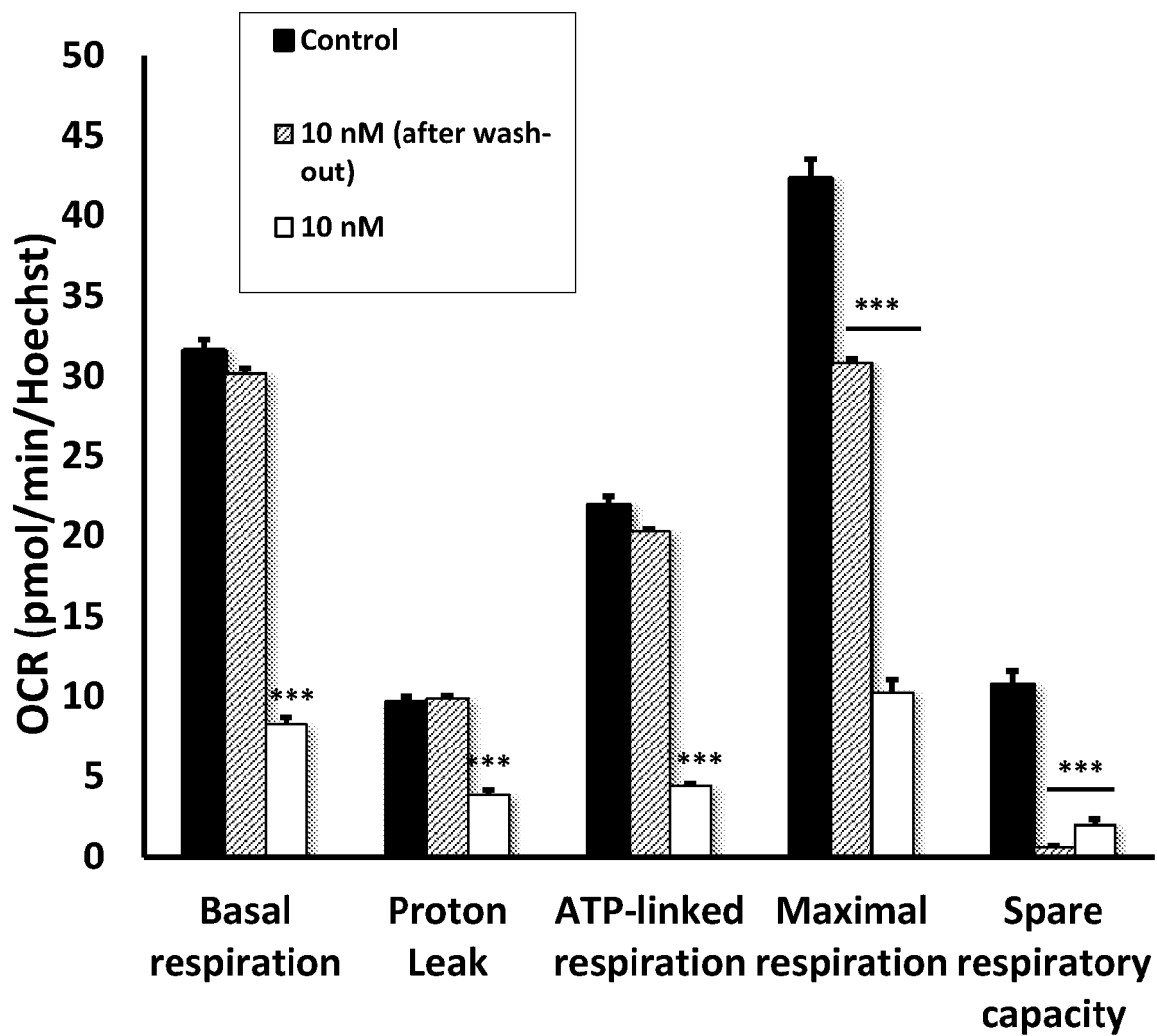
FIG. 13 shows the effects of DPI treatment, "wash-out", and recovery on basal respiration, proton leak, ATP-linked respiration, maximal respiration, and spare respiratory capacity.

The effects of DPI also may be highly reversible. To assess the reversibility of DPI's effects, MCF7 cells were first subjected to DPI treatment for 24 hours. Then, DPI was removed ("wash-out") and the cells were cultured for an additional 24 hours, to allow recovery. FIG. 12 shows that, at 10 nM DPI, there was a near complete recovery of basal respiration, approaching 100%, after only 24 hours (FIG. 12C). Higher concentrations showed significant recovery, though the recovery was not as complete. Similarly, FIG. 13 shows near-complete or complete recovery for basal respiration, proton leak, ATP-linked respiration, and maximal respiration, for 10 nM DPI and the 10 nM after "wash-out" populations.

Figure 14A:
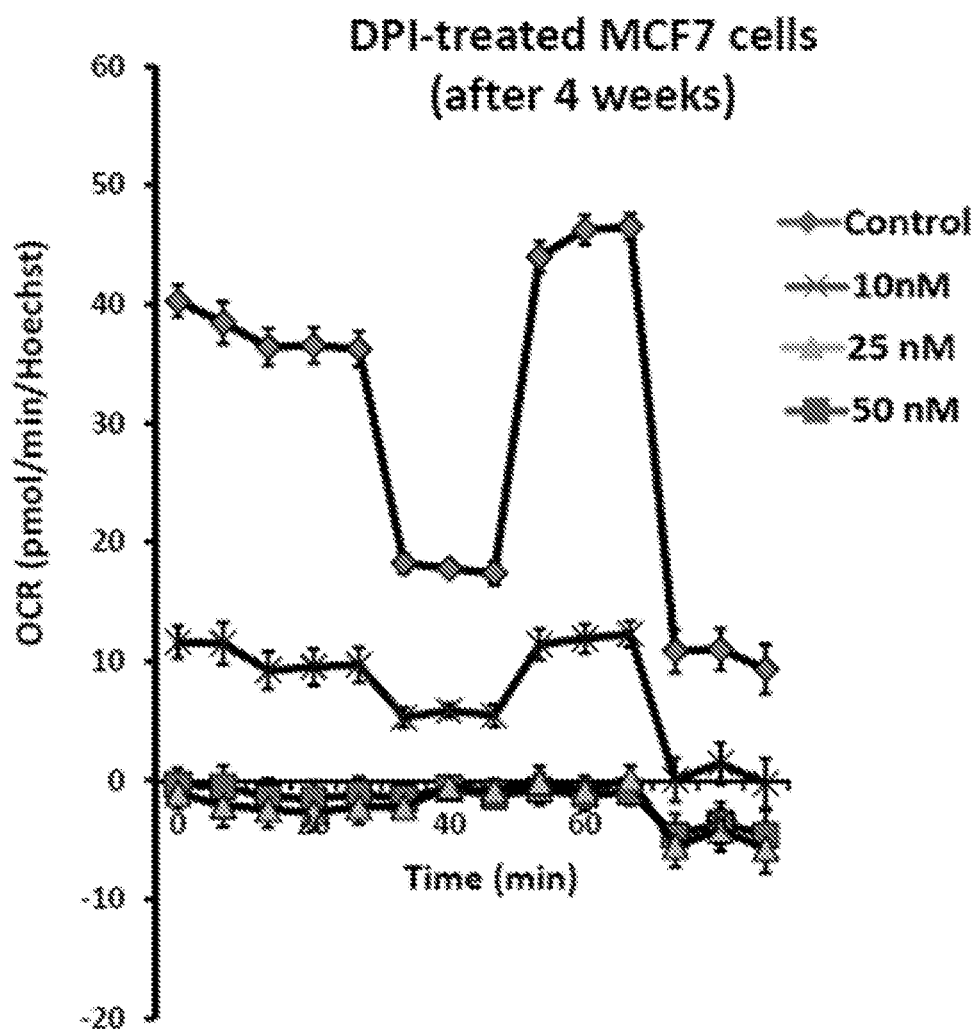
FIG. 14A shows the effects of long-term treatment with DPI on OCR.
Figure 14B:
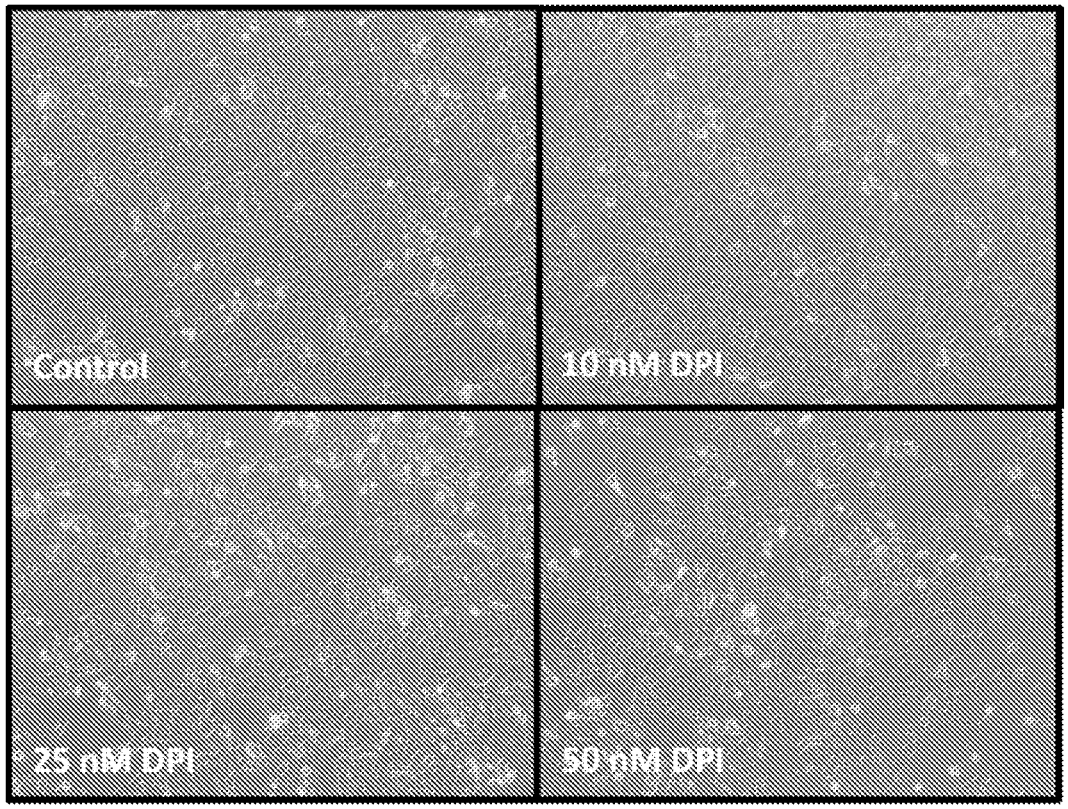
FIG. 14B shows the effects of long-term treatment with DPI on the morphology and density of MCF7 cells.

The inventors also examined the effects of long-term treatment with DPI on cells. MCF7 cells were cultured for 1 month in the presence of varying concentrations of DPI (10, 25, and 50 nM). Then, mitochondrial respiration was assessed. FIG. 14A illustrates that these concentrations all show near complete inhibition of respiration. At a DPI concentration of 10 nM, the morphology and density of the cells remains unchanged (FIG. 14B).

Figure 15:
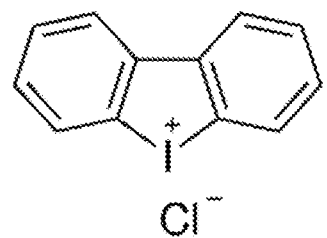
FIG. 15 shows a comparison of the structure of compound A, DPI, and compound B, flavin mononucleotide (FMN).
Figure 15:
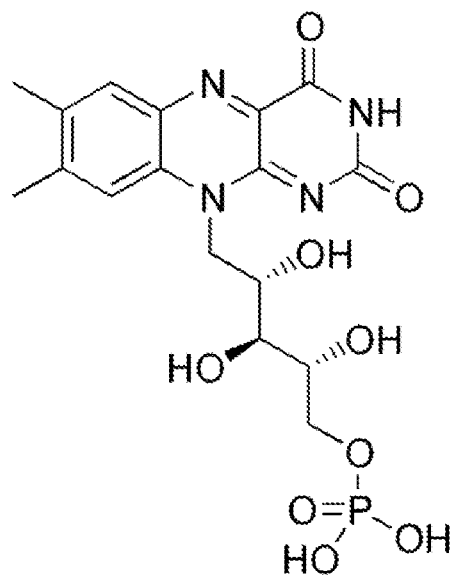
Figure 16:
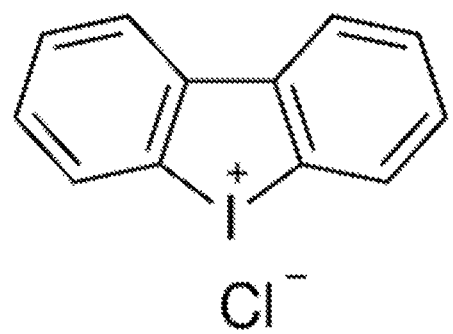
FIG. 16 compares the structure of compound A, DPI, and the related compound B, diphenyliodonium chloride.
Figure 16:
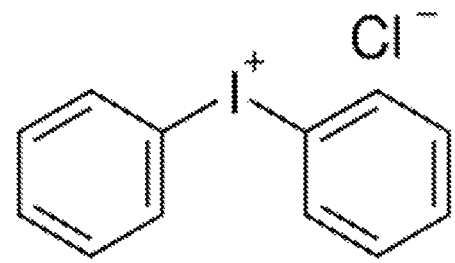
Figure 17:
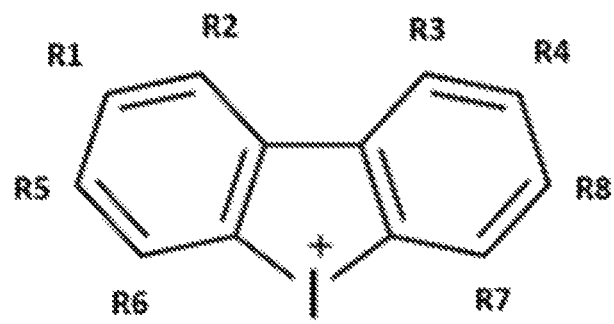
FIG. 17 shows possible locations for the attachment of functional R groups that may be added to DPI and DPI-related compounds to target mitochondria.
Figure 17:
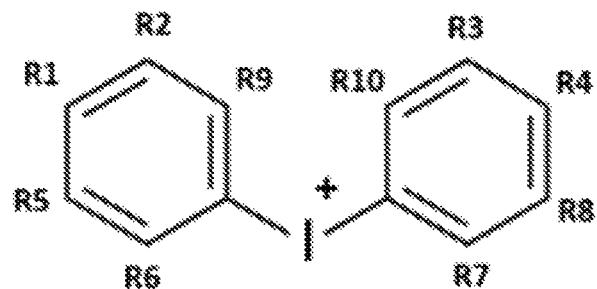

The inventors hypothesize that DPI blocks mitochondrial respiration by inhibiting flavin-containing enzymes (flavin mononucleotide (FMN), flavin adenine dinucleotide (FAD), and riboflavin). A comparison of the structures of (A) DPI and (B) FMN are shown in FIG. 15. Flavin-containing enzymes include three protein components of mitochondrial Complex I—NDUFV1 (51 kD), NDUFV2 (24 kD) and NDUFV3 (10 kD). SDHA is also a flavo-protein that is part of both mitochondrial Complex II and the Krebs cycle. Using GeneCards® as a bioinformatic reference tool, inventors estimate that ~70% of all flavin-containing gene products are localized to the mitochondria (Weizmann Institute of Science, Rehovot, Ill.). As such, inventors hypothesize DPI acts by inhibiting the mitochondria at Complex I and II. Actions of DPI may be via the induction of a mitochondrial deficiency in FMN and/or FAD, and/or by inactivating flavin-containing enzymes in CSCs. The inventors therefore expect that DPI, analogues of DPI, and DPI-related compounds (e.g., Diphenyliodonium chloride), may be used to treat CSCs (see, e.g., FIG. 17). It should be appreciated that methods disclosed herein may be used to screen and validate such compounds for pharmaceutical efficacy, including, for example, anti-cancer activity, anti-aging activity, radiosensitizing activity, photosensitizing activity.

Figure 18:
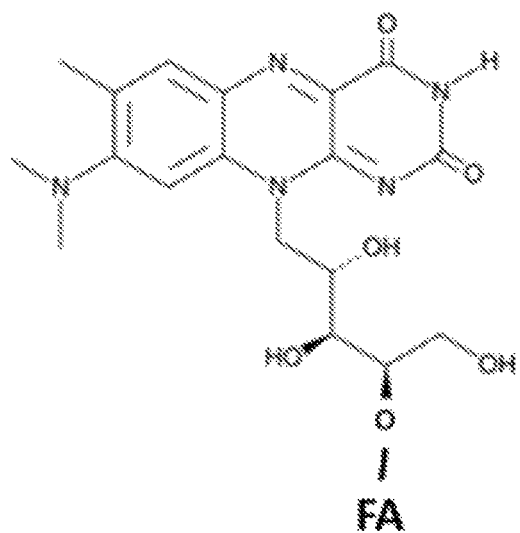
FIG. 18 shows examples of mitoflavin compounds, derivatives of riboflavin that inhibit mitochondrial function.
Figure 18:
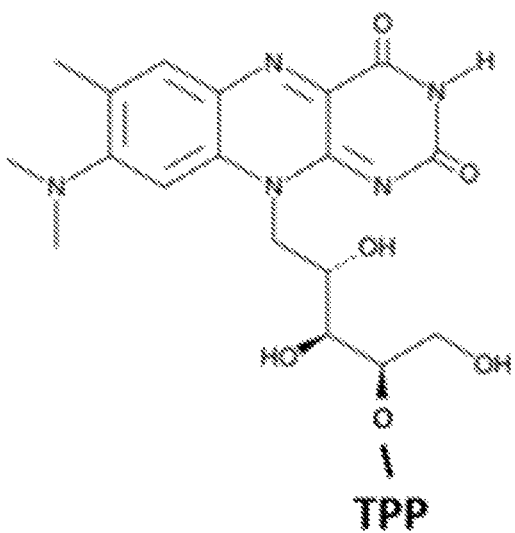

In some embodiments, mitoflavoscins may be designed to target mitochondria by attachment of at least one membrane-targeting signal and/or at least one mitochondrial-targeting signal. Under the present approach, a compound may be modified with a targeting signal that increases the compound's specificity towards mitochondria. For example, FIG. 18 shows locations for the attachment of functional R groups that may be added to DPI or DPI-related compounds to target mitochondria. In some embodiments, the membrane-targeting signal includes fatty acids such as palmitic acid, stearic acid, myristic acid, and oleic acid. It should be appreciated that this is not a comprehensive list of membrane-targeting signals, and that an unlisted membrane-targeting signal may be used without departing from the present approach. In some embodiments, the mitochondrial-targeting signal includes triphenyl-phosphonium (TPP), guanidinium-based moieties, and choline esters. It should be appreciated that this is not a comprehensive list of mitochondrial-targeting signals, and that an unlisted mitochondrial-targeting signal may be used without departing from the present approach.

It should be appreciated that the functional R groups shown in FIG. 18 may be the same or different and may be selected from any of: hydrogen, carbon, nitrogen, sulfur, oxygen, fluorine, chlorine, bromine, iodine, carboxyl, alkanes, cyclic alkanes, alkane-based derivatives, alkenes, cyclic alkenes, alkene-based derivatives, alkanes, alkane-based derivative, ketones, ketone-based derivatives, aldehydes, aldehyde-based derivatives, carboxylic acids, carboxylic acid-based derivatives, ethers, ether-based derivatives, esters and ester-based derivatives, amines, amino-based derivatives, amides, amide-based derivatives, monocyclic or polycyclic arene, heteroarenes, arene-based derivatives, heteroarene-based derivatives, phenols, phenol-based derivatives, benzoic acid, benzoic acid-based derivatives, and one or more mitochondrial targeting signals, among other functional groups later identified. For clarification, mitochondrial targeting signals are defined as any chemical or peptide entity that increases the efficiency of targeting the attached molecule to the mitochondria. Such modification would be expected to increase the potency and effectiveness of a compound. Thus, R may be any mitochondrial targeting signal (peptide or chemical), including cationic compounds, such as tri-phenyl-phosphonium (TPP), a guanidinium-based moiety and/or choline esters, among others.

Since DPI targets flavin-containing enzymes, its effects on mitochondrial function may be explained by the pharmacological induction of an acute Riboflavin (Vitamin B2) deficiency. Riboflavin is the biochemical precursor of FAD and FMN. Previous studies have shown that, when mammalian HepG2 cells were cultured in Riboflavin-free media, key components of mitochondrial complex I (NDUFS1; NDUFV2) and complex II (SDHA) were significantly reduced (by up to 5-fold), as were many other mitochondrial-related proteins, such as AIFM1, DLD, MCAD and NQO1. Previous data has also shown that flavins are autofluorescent markers of increased mitochondrial power and elevated CSC activity. Thus, DPI, analogues of DPI, and DPI-related compounds may be used to treat CSCs by targeting flavins.

Because DPI may eradicate CSCs through inhibition of mitochondrial respiration via the acute and reversible induction of a flavin-deficiency (likely FMN), inventors hypothesize that mechanism(s) for acutely inducing a riboflavin-deficiency may also be useful for therapeutically eradicating CSCs. Another method to induce an acute riboflavin deficiency may be to use "dominant-negative" derivatives of riboflavin. These riboflavin derivatives could also be enhanced by the addition of chemical groups to increase their potency. For example, Roseoflavin [8-Demethyl-8-(dimethylamino)-riboflavin or 8-Dimethylaminoriboflavin] is a naturally occurring anti-bacterial compound that is a derivative of riboflavin, which can be chemically modified to optimize its potential for targeting CSCs. Lumichrome (7,8-Dimethylalloxazine) is a fluorescent photoproduct of riboflavin degradation, which also can be chemically modified to optimize its potential for targeting CSCs. Other common derivatives of riboflavin include: Alloxazine, Lumiflavine, 1,5-dihydroribollavin and 1,5-dihydroflavin. These derivatives of riboflavin may be modified to increase their efficiency for targeting to mitochondria by the addition of a membrane-targeting signal or mitochondrial-targeting signal, such as i) a fatty acid moiety or ii) a TPP (triphenyl phosphonium) moiety. These mitochondrially-targeted entities may be tell fed "mitoflavins," compounds that are derivatives of riboflavin that inhibit mitochondrial function. Examples of mitoflavins are provided in FIG. 18, wherein FA denotes a fatty acid moiety and TPP denotes a triphenyl phosphonium moiety.

The inventors hypothesize an additional mechanism for DPI's effects on mitochondria is inhibition of ROS production (i.e., superoxide anion), by preventing reverse electron transport from succinate at mitochondrial Complex I, and without affecting forward electron transport. DPI prevents the production of an unwanted side reaction, which contributes to unnecessary ROS production and cellular damage, during mitochondrial respiration.

Additional evidence shows that targeting the metabolism of other vitamins can be used as a cancer treatment strategy. Anti-folates are anti-metabolites that block or disrupt the actions of folate. Most anti-folate drugs exert their effects by targeting dihydrofolate reductase (DHFR). Folate serves as a co-factor for many biosynthetic enzymes (i.e., methyltransferases) that drive methionine, serine, purine and thymidine biosynthesis. Examples of FDA-approved anti-folate drugs include: Methotrexate; Pemetrexed; Proguanil; Pyrimethamine; and Trimethoprim. The actions of antifolates preferentially target rapidly dividing cells, especially during DNA-synthesis (the S-phase of the cell cycle). Currently, Methotrexate and Pemetrexed are routinely used for the treatment of various cancer types, such as osteosarcoma, non-small cell lung carcinoma, mesothelioma and hematologic malignancies. Therefore, anti-folate therapy is considered as a successful strategy for treating cancer and various infectious parasitic diseases, such as malaria, toxoplasmosis and *pneumocystis* pneumonia. However, anti-folates also have significant side effects, because they also affect the proliferation of normal cells, leading to nausea, vomiting, abdominal pain, agranulocytosis and aplastic anemia (bone marrow suppression). Targeting flavins with DPI, analogues of DPI, and DPI-related compounds (e.g., Diphenyliodonium chloride) may provide improved outcomes over these current treatments.

Mitochondria have been directly implicated in the process of aging. However, their exact role remains a hotly-debated topic. Inventors hypothesize that DPI may be used to keep normal cells in a state of metabolic-quiescence or "suspended animation", akin to hibernation, which might be extremely useful in slowing or reversing the aging process. In support of this assertion, previous studies in *C. elegans* have shown that DPI prevents the accumulation of lipofuscin (an aging-associated by-product or marker), during the response to oxidative stress.

The terminology used in the description of the invention herein is for the purpose of describing particular embodiments only and is not intended to be limiting of the invention. As used in the description of the invention and the appended claims, the singular forms "a," "an" and "the" are intended to include the plural forms as well, unless the context clearly indicates otherwise. The invention includes numerous alternatives, modifications, and equivalents as will become apparent from consideration of the following detailed description.

It will be understood that although the terms "first," "second," "third," "a)," "b)," and "c)," etc. may be used herein to describe various elements of the invention should not be limited by these terms. These terms are only used to distinguish one element of the invention from another. Thus, a first element discussed below could be termed a element aspect, and similarly, a third without departing from the teachings of the present invention. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measurable value may include any other range and/or individual value therein.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A mitoflavoscin having at least one fatty acid membrane-targeting signal selected from the group consisting of palmitic acid, stearic acid, myristic acid, and oleic acid.

2. The mitoflavoscin of claim 1, wherein the mitoflavoscin comprises at least one of diphenyleneiodonium having at least one fatty acid membrane-targeting signal, a pharmaceutically acceptable salt of diphenyleneiodonium having at least one fatty acid membrane-targeting signal, diphenyliodonium having at least one fatty acid membrane-targeting signal, and a pharmaceutically acceptable salt of diphenyliodonium having at least one fatty acid membrane-targeting signal.

3. The mitoflavoscin of claim 1, wherein the mitoflavoscin possesses at least one of anti-cancer activity, anti-aging activity, radiosensitizing activity, photosensitizing activity.

4. The mitoflavoscin of claim 2, wherein the mitoflavoscin possesses at least one of anti-cancer activity, anti-aging activity, radiosensitizing activity, photosensitizing activity.

5. The mitoflavoscin of claim 1, wherein the mitoflavoscin sensitizes cancer cells to at least one of chemotherapeutic agents, natural substances, and calorie restriction.

6. The mitoflavoscin of claim 2, wherein the mitoflavoscin sensitizes cancer cells to at least one of chemotherapeutic agents, natural substances, and caloric restriction.

7. The mitoflavoscin of claim 1, wherein the at least one fatty acid membrane-targeting signal is myristic acid.

8. The mitoflavoscin of claim 2, wherein the at least one fatty acid membrane-targeting signal is myristic acid.

9. The mitoflavoscin of claim 1, wherein the mitoflavoscin binds to at least one of Flavin adenine dinucleotide and Flavin mononucleotide.

10. The mitoflavoscin of claim 8, wherein the mitoflavoscin binds to at least one of Flavin adenine dinucleotide and flavin mononucleotide.

11. The mitoflavoscin of claim 1, wherein the mitoflavoscin further comprises a mitochondria-targeting compound.

12. The mitoflavoscin of claim 11, wherein the mitoschondia-targeting compound is at least one compound selected from the group comprising a second membrane targeting signal and a mitochondrial ribosome-targeting signal.

13. The mitoflavoscin of claim 12, wherein the second membrane targeting signal is selected from palmitic acid, stearic acid, myristic acid, and oleic acid.

14. The mitoflavoscin of claim 12, wherein the mitochondrial targeting signal is a compound selected from the group comprising tri-phenyl-phosphonium and guanidinium.

15. The mitoflavoscin of claim 2, wherein the mitoflavoscin comprises diphenyleneiodonium having at least one fatty acid membrane-targeting signal, and the targeting signal comprises myristic acid.

16. A pharmaceutical composition comprising, as the active ingredient, at least one mitoflavoscin, wherein the mitoflavoscin has at least one fatty acid membrane-targeting signal selected from the group consisting of palmitic acid, stearic acid, myristic acid, and oleic acid.

17. The pharmaceutical composition of claim 16, wherein the at least one mitoflavoscin comprises at least one of diphenyleneiodonium having at least one fatty acid membrane-targeting signal, a pharmaceutically acceptable salt of diphenyleneiodonium having at least one fatty acid membrane-targeting signal, diphenyliodonium having at least one fatty acid membrane-targeting signal, and a pharmaceutically acceptable salt of diphenyliodonium having at least one fatty acid membrane-targeting signal.

18. The pharmaceutical composition of claim 16, wherein the composition is labelled for at least one of treating a cancer, treating a bacterial infection, treating a pathogenic yeast infection, treating an age-related condition, and reducing the effects of aging.

19. The pharmaceutical composition of claim 17, wherein the mitoflavoscin comprises diphenyleneiodonium having at least one fatty acid membrane-targeting signal, and the targeting signal comprises myristic acid.

* * * * *